United States Patent
Page et al.

(10) Patent No.: US 7,465,543 B1
(45) Date of Patent: Dec. 16, 2008

(54) MULTIPLEX DNA IDENTIFICATION OF CLINICAL YEASTS USING FLOW CYTOMETRY

(75) Inventors: Brent T. Page, Peoria, IL (US); Cletus P. Kurtzman, Peoria, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 372 days.

(21) Appl. No.: 11/134,157

(22) Filed: May 20, 2005

Related U.S. Application Data

(60) Provisional application No. 60/573,753, filed on May 21, 2004.

(51) Int. Cl.
- C12Q 1/68 (2006.01)
- C12Q 1/04 (2006.01)
- C12Q 1/02 (2006.01)
- C12Q 1/00 (2006.01)
- C12Q 1/24 (2006.01)

(52) U.S. Cl. .................. 435/6; 435/4; 435/34; 435/29; 435/30; 435/255.1

(58) Field of Classification Search .............. 435/6, 435/4, 34, 29, 30, 255.1
See application file for complete search history.

(56) References Cited

U.S. PATENT DOCUMENTS

| | | |
|---|---|---|
| 5,981,180 A | 11/1999 | Chandler et al. |
| 6,268,222 B1 | 7/2001 | Chandler |
| 6,514,295 B1 | 2/2003 | Chandler et al. |
| 6,528,165 B2 | 3/2003 | Chandler |
| 6,632,526 B1 | 10/2003 | Chandler et al. |
| 6,649,414 B1 | 11/2003 | Chandler et al. |

OTHER PUBLICATIONS

Oliveira et al., Differentiation of *Candida albicans* and *Candida dubliniensis* by fluorescent in situ hybridization with peptide nucleic acid probes.J Clin Microbiol. Nov. 2001;39(11):4138-41.*

JR Wingard -Importance of *Candida* species other than *C. albicans* as pathogens in oncology patients. Clin Infect Dis. Jan. 1995;20(1):115-25.*

Boktour MR etal., Multiple-species candidemia in patients with cancer.Cancer. Oct. 15, 2004;101(8):1860-5.*

Kurtzman, Cletus P., et al., "Phylogenetic relationships among yeasts of the '*Saccharomyces* complex' determined from multigene sequence analyses", FEMS Yeast Research, 3, 2003, pp. 417-432.

Kurtzman, C. P., et al., "Identification of Clinically Important Ascomycelous Yeasts Based on Nucleotide Divergence in the 5' End of the Large-Subunit (26S) Ribosomal DNA Gene", Journal of Clinical Microbiology, May 1997, vol. 35, No. 5, pp. 1216-1223.

Mannarelli, B.M., et al., "Rapid Identification of *Candida albicans* and Other Human Pathogenic Yeasts by Using Short Oligonucleotides in a PCR", Journal of Clinical Microbiology, Jun. 1998, vol. 36, No. 6, pp. 1634-1641.

* cited by examiner

*Primary Examiner*—Anne Marie S Wehbe
*Assistant Examiner*—Maria Leavitt
(74) *Attorney, Agent, or Firm*—John Fado; Randall E. Deck; Lesley Shaw

(57) ABSTRACT

Oligonucleotide probes that are specific for pathogenic yeasts and which may be used for the detection of such yeasts in biological samples are described. These probes are specific for yeast species within the clade of *Candida albicans* and other pathogenic ascomycetous yeasts, and may be used singly or in a multiplex hybridization assay system.

22 Claims, No Drawings

SEQUENCE LISTING

<160> NUMBER OF SEQ ID NOS: 45

<210> SEQ ID NO 1
<211> LENGTH: 21

-continued

```
<212> TYPE: DNA
<213> ORGANISM: Candida albicans

<400> SEQUENCE: 1
tattttgcat gctgctctct c                                              21

<210> SEQ ID NO 2
<211> LENGTH: 21
<212> TYPE: DNA
<213> ORGANISM: Candida dubliniensis

<400> SEQUENCE: 2
tattttgcaa gttactcttt c                                              21

<210> SEQ ID NO 3
<211> LENGTH: 21
<212> TYPE: DNA
<213> ORGANISM: Candida parapsilosis

<400> SEQUENCE: 3
cggtaggata agtgcaaaga a                                              21

<210> SEQ ID NO 4
<211> LENGTH: 21
<212> TYPE: DNA
<213> ORGANISM: Candida glabrata

<400> SEQUENCE: 4
ttgcctctcg tgggcttggg a                                              21

<210> SEQ ID NO 5
<211> LENGTH: 20
<212> TYPE: DNA
<213> ORGANISM: Candida natalensis

<400> SEQUENCE: 5
tggtattttg cgatcctttc                                                20

<210> SEQ ID NO 6
<211> LENGTH: 20
<212> TYPE: DNA
<213> ORGANISM: Pichia guilliermondii

<400> SEQUENCE: 6
atcagactcg atattttgtg                                                20

<210> SEQ ID NO 7
<211> LENGTH: 17
<212> TYPE: DNA
<213> ORGANISM: Candida tropicalis

<400> SEQUENCE: 7
gaattgcgtt ggaatgt                                                   17

<210> SEQ ID NO 8
<211> LENGTH: 21
<212> TYPE: DNA
<213> ORGANISM: Candida sp. Y-17456

<400> SEQUENCE: 8
gggcggtagg acaattgcaa a                                              21

<210> SEQ ID NO 9
```

```
<211> LENGTH: 20
<212> TYPE: DNA
<213> ORGANISM: Candida lodderae

<400> SEQUENCE: 9
ggacaatcgc gcgggaatgt                                              20

<210> SEQ ID NO 10
<211> LENGTH: 20
<212> TYPE: DNA
<213> ORGANISM: Candida neerlandica

<400> SEQUENCE: 10
aggagaatcg cttgggaacg                                              20

<210> SEQ ID NO 11
<211> LENGTH: 19
<212> TYPE: DNA
<213> ORGANISM: Candida sojae

<400> SEQUENCE: 11
agccttcgta gatgccagc                                               19

<210> SEQ ID NO 12
<211> LENGTH: 20
<212> TYPE: DNA
<213> ORGANISM: Candida mannitofaciens

<400> SEQUENCE: 12
tatagccact gtcgatactg                                              20

<210> SEQ ID NO 13
<211> LENGTH: 20
<212> TYPE: DNA
<213> ORGANISM: Lodderomyces elongisporus

<400> SEQUENCE: 13
atgagatgtc tagatctatg                                              20

<210> SEQ ID NO 14
<211> LENGTH: 20
<212> TYPE: DNA
<213> ORGANISM: Candida krusei

<400> SEQUENCE: 14
tggagtctgt gtggaaggcg                                              20

<210> SEQ ID NO 15
<211> LENGTH: 20
<212> TYPE: DNA
<213> ORGANISM: Candida zelanoides

<400> SEQUENCE: 15
ggtaactttg gttttggctc                                              20

<210> SEQ ID NO 16
<211> LENGTH: 20
<212> TYPE: DNA
<213> ORGANISM: Candida haemulonii

<400> SEQUENCE: 16
ggcgccagcg cgcagccaag                                              20
```

```
<210> SEQ ID NO 17
<211> LENGTH: 20
<212> TYPE: DNA
<213> ORGANISM: Candida haemulonii Type II

<400> SEQUENCE: 17
gccttgcgca accaaatcta                                               20

<210> SEQ ID NO 18
<211> LENGTH: 20
<212> TYPE: DNA
<213> ORGANISM: candida neerlandica

<400> SEQUENCE: 18
ttggtatttt gtatgttact                                               20

<210> SEQ ID NO 19
<211> LENGTH: 20
<212> TYPE: DNA
<213> ORGANISM: candida neerlandica

<400> SEQUENCE: 19
cttggaacag aacgtcacag                                               20

<210> SEQ ID NO 20
<211> LENGTH: 20
<212> TYPE: DNA
<213> ORGANISM: Candida albicans

<400> SEQUENCE: 20
atctttgggc ccggctcttg                                               20

<210> SEQ ID NO 21
<211> LENGTH: 24
<212> TYPE: DNA
<213> ORGANISM: Candida albicans

<400> SEQUENCE: 21
gcatatcaat aagcggagga aaag                                          24

<210> SEQ ID NO 22
<211> LENGTH: 19
<212> TYPE: DNA
<213> ORGANISM: Candida albicans

<400> SEQUENCE: 22
ggtccgtgtt tcaagacgg                                                19

<210> SEQ ID NO 23
<211> LENGTH: 20
<212> TYPE: DNA
<213> ORGANISM: Candida albicans

<400> SEQUENCE: 23
tagcctctga cgatactgcc                                               20

<210> SEQ ID NO 24
<211> LENGTH: 21
<212> TYPE: DNA
<213> ORGANISM: Candida albicans

<400> SEQUENCE: 24
acctaggatg ttggcataat g                                             21
```

```
<210> SEQ ID NO 25
<211> LENGTH: 20
<212> TYPE: DNA
<213> ORGANISM: Candida lodderae

<400> SEQUENCE: 25
ttggtatttt gcatgttgct                                               20

<210> SEQ ID NO 26
<211> LENGTH: 19
<212> TYPE: DNA
<213> ORGANISM: Candida tropicalis

<400> SEQUENCE: 26
gagaattgcg ttggaatgt                                                19

<210> SEQ ID NO 27
<211> LENGTH: 18
<212> TYPE: DNA
<213> ORGANISM: Lodderomyces elongisporus

<400> SEQUENCE: 27
agaattacgt tggaatgt                                                 18

<210> SEQ ID NO 28
<211> LENGTH: 19
<212> TYPE: DNA
<213> ORGANISM: Candida tropicalis

<400> SEQUENCE: 28
agaattgcgt tggaatgtg                                                19

<210> SEQ ID NO 29
<211> LENGTH: 18
<212> TYPE: DNA
<213> ORGANISM: Candida tropicalis

<400> SEQUENCE: 29
gaattgcgtt ggaatgtg                                                 18

<210> SEQ ID NO 30
<211> LENGTH: 20
<212> TYPE: DNA
<213> ORGANISM: Lodderomyces elongisporus

<400> SEQUENCE: 30
ggagaattgc gtaggaatgt                                               20

<210> SEQ ID NO 31
<211> LENGTH: 20
<212> TYPE: DNA
<213> ORGANISM: Candida haemulonii

<400> SEQUENCE: 31
gccggtccgc cttgcgcaac                                               20

<210> SEQ ID NO 32
<211> LENGTH: 20
<212> TYPE: DNA
<213> ORGANISM: Candida haemulonii

<400> SEQUENCE: 32
gccggtcccg gcgccagcgc                                               20
```

-continued

<210> SEQ ID NO 33
<211> LENGTH: 20
<212> TYPE: DNA
<213> ORGANISM: Candida sp.

<400> SEQUENCE: 33
ggacaattgc aaagaaatgt                                           20

<210> SEQ ID NO 34
<211> LENGTH: 20
<212> TYPE: DNA
<213> ORGANISM: Stephanoascus farinosus

<400> SEQUENCE: 34
ttggtttgta acgatcaact                                           20

<210> SEQ ID NO 35
<211> LENGTH: 20
<212> TYPE: DNA
<213> ORGANISM: Zygoascus hellenicus

<400> SEQUENCE: 35
aagggatcta aatcagacat                                           20

<210> SEQ ID NO 36
<211> LENGTH: 22
<212> TYPE: DNA
<213> ORGANISM: Candida haemulonii

<400> SEQUENCE: 36
aacgagcagt cgatgtagta ca                                        22

<210> SEQ ID NO 37
<211> LENGTH: 23
<212> TYPE: DNA
<213> ORGANISM: Candida haemulonii

<400> SEQUENCE: 37
aaagtgggag ctgatgtagc aac                                       23

<210> SEQ ID NO 38
<211> LENGTH: 19
<212> TYPE: DNA
<213> ORGANISM: candida krusei

<400> SEQUENCE: 38
gaggactgcg ccgtgtagg                                            19

<210> SEQ ID NO 39
<211> LENGTH: 20
<212> TYPE: DNA
<213> ORGANISM: Clavispora lusitaniae

<400> SEQUENCE: 39
cgggccagcg tcaaataaac                                           20

<210> SEQ ID NO 40
<211> LENGTH: 20
<212> TYPE: DNA
<213> ORGANISM: Pichia ciferrii

<400> SEQUENCE: 40

-continued

```
aagataatag cagttaaatg                                              20

<210> SEQ ID NO 41
<211> LENGTH: 17
<212> TYPE: DNA
<213> ORGANISM: Candida sojae

<400> SEQUENCE: 41
gccttcgtag atactgc                                                 17

<210> SEQ ID NO 42
<211> LENGTH: 20
<212> TYPE: DNA
<213> ORGANISM: Candida lodderae

<400> SEQUENCE: 42
gcggcaggac aatcgcgtgg                                              20

<210> SEQ ID NO 43
<211> LENGTH: 20
<212> TYPE: DNA
<213> ORGANISM: Candida albicans

<400> SEQUENCE: 43
gtgaaattgt tgaaagggaa                                              20

<210> SEQ ID NO 44
<211> LENGTH: 20
<212> TYPE: DNA
<213> ORGANISM: Pichia guilliermondii

<400> SEQUENCE: 44
gtgacccgca gcttatcggg                                              20

<210> SEQ ID NO 45
<211> LENGTH: 20
<212> TYPE: DNA
<213> ORGANISM: Lodderomyces elongisporus

<400> SEQUENCE: 45
tgcggcttcg gcctaggatg                                              20
```

MULTIPLEX DNA IDENTIFICATION OF CLINICAL YEASTS USING FLOW CYTOMETRY

BACKGROUND OF THE INVENTION

1. Field of the Invention

This invention relates to assays and kits for the identification of pathogenic yeasts from biological samples.

2. Description of the Prior Art

*Candida albicans*, other yeasts of the *C. albicans* clade, as well as many additional species, are of increasing importance as opportunistic pathogens in healthy as well as immunocompromised hosts. Many of these yeasts have no known sexual cycle and are endogenous organisms that can be isolated from numerous environmental sources, including the skin and mucosal tissues of persons whose immune systems are intact. However, perturbations of the immune or endocrine systems can create opportunities for *Candida* species to convert from a commensal state to invade tissues either locally or systemically. An example of this opportunism is the oral-esophageal or vaginal candidiasis that is encountered in physiologically stressed and in severely immunocompromised hosts such as those with HIV infections. *Candida albicans* is the most causative species of disseminated candidiasis followed by *C. tropicalis*, *C. parapsilosis*, and *C. glabrata* (Odds, Candida and Candidiasis: A Review and Bibliography, $2^{nd}$ ed., Bailere Tindall, Philadelphia, 1988). Dissemination occurs when the yeast is spread via the bloodstream or by invasion of mucosal surfaces to internal organs (Odds, 1988). High-risk patient populations include individuals with malignancy or neutropenia, those receiving chemotherapy and/or multiple antibiotics, and those with indwelling catheters or low birth weight infants (Armstrong, 1989, Rev. Infect. Dis., 2:S1591-S1599).

In *C. albicans*, the nuclear rDNA genes encoding the 5S, 18S, 5.8S, and 28S rRNAs are found as 50-100 copy tandem repeats of approximately 10 kb unit length on chromosome seven (Magee et al., 1987, J. Bacteriol., 169:1639-1643; Thrash-Bingham and Gorman, 1992, Curr. Genetics, 22:93-100). The 5S rDNA gene (121 bp) is flanked by two nontranscribed regions located between the small and large subunits, and collectively termed the intergenic spacer (IGS). In addition, sequence analysis of the ITS1/5.8S/ITS2 internally transcribed spacer (ITS) region has shown strain variation within at least one fungal species (O'Donnell, 1992, Curr. Genet., 22:213-220), while other species have demonstrated complete conservation (Mitchell et. al., 1992, J. Med. Vet. Mycol., 30:207-218). Strain-specific restriction fragment length polymorphisms (RFLPs) have previously been observed in the IGS region for *C. albicans* (Magee et al., ibid).

Traditionally, many yeast infections have been detected using conventional culture techniques for isolation of the causative agent from biological samples. However, culture-based identification of *Candida* species requires at least one day following initial positive results to obtain a pure culture, another day to identify *C. albicans* isolates by germ tube formation, and two or more additional days to identify non-albicans *Candida* isolates by API-20C sugar assimilation strip tests and cornmeal agar morphology.

More recently, techniques have been developed for the detection of bacterial and viral DNA from the bloodstream of infected patients through the use of the polymerase chain reaction (PCR). The PCR amplifies genomic DNA geometrically so that it may be detected by agarose gel electrophoresis, Southern blotting, or dot blot hybridization (Miyakawa et al., 1992, J. Clin. Micro., 30:894-900; Kafatos et al., 1979, Nucl. Acids Res., 3:1541-1552; Lasker et al., 1992, Clin. Infect. Dis., 15:223-233).

Use of polymerase chain reaction (PCR) based tests to detect *C. albicans* and other pathogenic yeast DNA in body fluids has produced some encouraging results. However, routine application of these tests for the detection of candidemia remains difficult. Current methods require labor-intensive sample preparation, costly enzymes for liberation of *Candida* DNA, and phenol-chloroform extraction to purify DNA before PCR amplification. After amplification, detection of PCR products by gel electrophoresis or Southern blotting is often not practical in a clinical laboratory setting. Sensitivity has been variable and false positive as well as false negative results have been reported. Moreover, most studies have concentrated on the detection of *C. albicans* DNA but not on DNA from non-albicans *Candida* species.

Despite the advances in the detection of yeast infections, the need remains for a test to rapidly and accurately identify *C. albicans* and other pathogenic yeasts of the *C. albicans* clade as well as other pathogenic species.

SUMMARY OF THE INVENTION

We have now discovered oligonucleotide probes that are specific for pathogenic yeasts and which may be used for the detection of such yeasts in biological samples. These probes are specific for yeast species within the clade of *Candida albicans* as well as other pathogenic ascomycetous yeasts, and may be used singly or in a multiplex hybridization assay system. In one such preferred multiplex system, pathogenic yeast species in a biological sample may be detected by:
  a) recovering nucleic acid from the sample suspected of containing a pathogenic yeast,
  b) contacting the nucleic acid with a plurality of the detectably labeled oligonucleotide probes under conditions effective to allow hybridization between the probes and complementary nucleic acids and form a probe/nucleic acid complex when one or more of the pathogenic yeasts are present, and
  c) detecting the presence or absence of probe/nucleic acid complexes as an indication of the presence of a pathogenic yeast.

The probes of this invention may also be provided in a kit.

In accordance with this discovery it is an object of this invention to provide oligonucleotide hybridization probes which are species-specific for yeasts within the clade of *Candida albicans* as well as other pathogenic ascomycetous yeasts.

Another object of this invention is to provide a plurality of hybridization probes which are suitable for use as a mixture in a multiplex assay system.

Yet another object of this invention is to provide a plurality of hybridization probes which are suitable for use as a mixture in a multiplex assay system without a significant degree of cross-reaction with other species or with each other.

Other objects and advantages of this invention will become readily apparent from the ensuing description.

DEFINITIONS

Clade refers to a group composed of species descended from a single common ancestor; a monophyletic group. As used herein, the clade of *Candida albicans* includes *Candida albicans, Candida dubliniensis, Candida parapsilosis, Lodderomyces elongisporus, Candida* sp. n. NRRL Y-17456,

*Candida lodderae, Candida viswanathii, Candida neerlandica, Candida sojae, Candida tropicalis,* and *Candida maltosa.* It is understood that *Candida* sp. N.Y.-17546 may encompass *C. metapsilosis* and *C. orthopsilosis* newly described by Tavanti et al. [2005, J. Clin. Microbiol, 43(1): 284-292].

Hybridization refers to the pairing together or annealing of single-stranded regions of nucleic acids to form double-stranded molecules. The region of double-strandedness can include the full-length of one or both of the single-stranded nucleic acids, or all of one single-stranded nucleic acid and a subsequence of the other single-stranded nucleic acid, or the region of double-strandedness can include a subsequence of each nucleic acid. An overview to the hybridization of nucleic acids is found in Tijssen (Laboratory Techniques in Biochemistry and Molecular Biology—Hybridization with Nucleic Acid Probes Part I, Chapter 2: "Overview of principles of hybridization and the strategy of nucleic acid probe assays", Elsevier, N.Y., 1993). Probes which specifically hybridize with a double-stranded nucleic acid are hybridizing with one of the two strands when in single-stranded form.

Nucleic acid refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence optionally includes the complementary sequence thereof.

An oligonucleotide probe is defined as a fragment of DNA or RNA whose nucleotide sequence has at least partial identity with the sequence of the target rDNA or rRNA so as to selectively bind to that rRNA or rDNA. Oligonucleotide probes include linear oligomers of natural or modified monomers or linkages, including deoxyribonucleosides, ribonucleosides, and the like, capable of specifically binding to a target nucleic acid. When the oligonucleotide is represented by a sequence of letters, such as "ATGC" it will be understood that the nucleotides are in 5' to 3' order from left to right and that "A" denotes deoxyadenosine, "C" denotes deoxycytidine, "G" denotes deoxyguanosine, "T" denotes thymidine, and "U" denotes uracil, unless otherwise noted.

Primer refers to an oligonucleotide, whether occurring naturally as in a purified restriction digest, or produced synthetically, which is capable of hybridizing to a strand of the target sequence. When the terminal 3' nucleotide has hybridized it acts as a point of initiation of synthesis under conditions in which synthesis of an extension of the primer is induced. These conditions typically include the presence of four different nucleotide triphosphates (a nucleotide reagent) and thermostable enzyme in an appropriate buffer and at a suitable temperature. When primer pairs are referred to herein, the pair is meant to include one primer which is capable of hybridizing to the sense strand of a double-stranded target nucleic acid (the sense primer) and one primer which is capable of hybridizing to the antisense strand of a double-stranded target nucleic acid (the antisense primer). The primer pair will be designed such that they flank the region of the target nucleic acid to be amplified and will cause the target region to be amplified when placed in an amplification protocol such as polymerase chain reaction.

Substantially homologous or substantially complementary probes or primers refer to a nucleotide sequence that is a polynucleotide or oligonucleotide containing naturally occurring nucleotides or their analogs, such as 7-diazoguanosine or inosine, sufficiently complementary to hybridize with the target sequence such that stable and specific binding occurs between the probe or primer and the target sequence. The degree of homology required for formation of a stable hybridization complex (duplex) varies with the stringency of the hybridization or amplification medium. The probe or primer should be substantially homologous to the target strands of each target sequence. This means that the probe or primer must be sufficiently complementary to hybridize with the appropriate strand under standard hybridization or amplification conditions. Therefore, the probe or primer sequence need not reflect the exact sequence of the template. For example, a noncomplementary nucleotide fragment may be attached to the 5' end of a primer, with the remainder of the primer sequence complementary to the strand. Alternatively, noncomplementary bases or longer sequences can be interspersed into the primer provided that the primer sequence has sufficient complementarity with the sequence of the target sequence to hybridize with it and thereby form a template for synthesis of the extension product.

DETAILED DESCRIPTION OF THE INVENTION

The oligonucleotide probes of this invention hybridize to rRNA or, preferably, rDNA from the D1/D2 region of the 28S ribosomal subunit. As described in greater detail hereinbelow, a first set of probes are provided which are specific for various species of the *C. albicans* clade as well as other pathogenic ascomycetous yeasts, i.e., the probes specifically hybridize to the rDNA or rRNA of the target species under stringent hybridizing conditions without binding to other related microorganisms, except as noted. A second set of probes are provided which recognize a number of different species within the clade under stringent hybridizing conditions.

The probes of the invention specifically hybridize with individual species or clades and result in the specific isolation of the targeted sequence. The nucleotide sequences of the probes are as follows:

Alb7 comprises at least 19 consecutive bases of the sequence TATTTTGCATGCTGCTCTCTC (SEQ ID no. 1), Dub5 comprises at least 19 consecutive bases of the sequence TATTTTGCAAGTTACTCTTTC (SEQ ID no. 2), Parap2B comprises at least 18 consecutive bases of the sequence CGGTAGGATAAGTGCAAAGAA (SEQ ID no. 3), Glab5 comprises at least 19 consecutive bases of the sequence TTGCCTCTCGTGGGCTTGGGA (SEQ ID no. 4), Hanclade3 comprises at least 18 consecutive bases of the sequence TGGTATTTTGCGATCCTTTC (SEQ ID no. 5), GG2 comprises at least 18 consecutive bases of the sequence ATCAGACTCGATATTTTGTG (SEQ ID no. 6), Trop6 comprises at least 15 consecutive bases of the sequence GAATTGCGTTGGAATGT (SEQ ID no. 7), SP1 comprises at least 19 consecutive bases of the sequence GGGCGGTAGGACAATTGCAAA (SEQ ID no. 8), Lod2 comprises at least 18 consecutive bases of the sequence GGACAATCGCGCGGGAATGT (SEQ ID no. 9), Nee5 comprises at least 18 consecutive bases of the sequence AGGAGAATCGCTTGGGAACG (SEQ ID no. 10), Soj7 comprises at least 17 consecutive bases of the sequence AGCCTTCGTAGATGCCAGC (SEQ ID no. 11), Malt5 comprises at least 18 consecutive bases of the sequence TATAGCCACTGTCGATACTG (SEQ ID no. 12), Lelon7 comprises at least 18 consecutive bases of the sequence ATGAGATGTCTAGATCTATG (SEQ ID no. 13), Krusei5 comprises at least 18 consecutive bases of the sequence TGGAGTCTGTGTGGAAGGCG (SEQ ID no. 14), Zeyla7 comprises at least 18 consecutive bases of the sequence GGTAACTTTGGTTTTGGCTC (SEQ ID no. 15), HaemtI3 comprises at least 18 consecutive bases of the sequence GGCGCCAGCGCGCAGCCAAG (SEQ ID no. 16), HaemtII3 comprises at least 18 consecutive bases of the sequence GCCTTGCGCAACCAAATCTA (SEQ ID no. 17), Albclade5 comprises at least 18 consecutive bases of the sequence TTGGTATTTTGTATGTTACT (SEQ ID no. 18), Albclade3 comprises at least 18 consecutive bases of the sequence CTTGGAACAGAACGTCACAG (SEQ ID no. 19), Albclade4 comprises at least 18 consecutive bases of the sequence ATCTTTGGGCCCGGCTCTTG (SEQ ID no. 20), Albclade8 comprises at least 18 consecutive bases of the sequence TAGCCTCTGACGATACTGCC (SEQ ID no. 23), Albclade9 comprises at least 19 consecutive bases of the sequence ACCTAGGATGTTGGCATAATG (SEQ ID no. 24), Albclade10 comprises at least 18 consecutive bases of the sequence TTGGTATTTTGCATGTTGCT (SEQ ID no. 25), Trop4 comprises at least 17 consecutive bases of the sequence GAGAATTGCGTTGGAATGT (SEQ ID no. 26), Trop5B comprises at least 16 consecutive bases of the sequence AGAATTACGTTGGAATGT (SEQ ID no. 27), Trop8 comprises at least 17 consecutive bases of the sequence AGAATTGCGTTGGAATGTG (SEQ ID no. 28), Trop9 comprises at least 16 consecutive bases of the sequence GAATTGCGTTGGAATGTG (SEQ ID no. 29), Lelon2 comprises at least 18 consecutive bases of the sequence GGAGAATTGCGTAGGAATGT (SEQ ID no. 30), Hem22 comprises at least 18 consecutive bases of the sequence GCCGGTCCGCCTTGCGCAAC (SEQ ID no. 31), Hem12 comprises at least 18 consecutive bases of the sequence GCCGGTCCCGGCGCCAGCGC (SEQ ID no. 32), and SP12 comprises at least 18 consecutive bases of the sequence GGACAATTGCAAAGAAATGT (SEQ ID no. 33).

Fari2 comprises at least 18 consecutive bases of the sequence TTGGTTTGTAACGATCAACT (SEQ ID no. 34).

Hellen2 comprises at least 18 consecutive bases of the sequence AAGGGATCTAAATCAGACAT (SEQ ID no. 35).

HemC comprises at least 18 consecutive bases of the sequence AACGAGCAGTCGATGTAGTACA (SEQ ID no. 36).

HemIIB comprises at least 18 consecutive bases of the sequence AAAGTGGGAGCTGATGTAGCAAC (SEQ ID no. 37).

KrusF comprises at least 18 consecutive bases of the sequence GAGGACTGCGCCGTGTAGG (SEQ ID no. 38).

Lusit2 comprises at least 18 consecutive bases of the sequence CGGGCCAGCGTCAAATAAAC (SEQ ID no. 39).

Pcifer3 comprises at least 18 consecutive bases of the sequence AAGATAATAGCAGTTAAATG (SEQ ID no. 40).

SojC comprises at least 15 consecutive bases of the sequence GCCTTCGTAGATACTGC (SEQ ID no. 41).

VisA comprises at least 18 consecutive bases of the sequence GCGGCAGGACAATCGCGTGG (SEQ ID no. 42).

UniD comprises at least 18 consecutive bases of the sequence GTGAAATTGTTGAAAGGGAA (SEQ ID no. 43).

GG3 comprises at least 18 consecutive bases of the sequence GTGACCCGCAGCTTATCGGG (SEQ ID no. 44).

LPW comprises at least 18 consecutive bases of the sequence TGCGGCTTCGGCCTAGGATG (SEQ ID no. 45).

Although the probes include slightly shorter fragments of the above mentioned sequences (i.e., a total of 1 or 2 bases may be omitted from the 5' and/or 3' end), in the preferred embodiment the entire sequences are used as the probes. It is also understood that oligonucleotides which are complimentary to any or all of the above-mentioned SEQ ID nos. 1-20 and 23-45 are also suitable for use herein. It is further understood that when using probes for rRNA rather than rDNA, any thymidine in the probe sequences will be replaced with uracil. Moreover, the invention also encompasses modifications to the probes, including substantially homologous probes, as long as their specificity (species or clade) is maintained. Similarly, oligonucleotides used as probes can have base substitutions so long as enough complementary bases exist for specific hybridization (Kunkel et al., Methods Enzymol., 154:367, 1987).

Of the above-mentioned probes, the following are species- or clade-specific:

Alb7 recognizes *Candida albicans* only,

Dub5 recognizes *Candida dubliniensis* only,

Parap2B and LPW together recognize *Candida parapsilosis* only,

Glab5 recognizes *Candida glabrata* only,

LPW (or less preferably Lelon7) and Trop5B together recognize *Lodderomyces elongisporus* only, SP1 and SP12 recognize *Candida* sp. n. NRRL Y 17456 only, VisA, and to a lesser extent Lod2, recognize *Candida lodderae* and *Candida viswanathii*, Nee5 recognizes *Candida neerlandica* only, KrusF, and to a lesser extent Krusei5, recognize *Candida krusei* only, GG2 and GG3 together recognize *Pichia (Candida) guilliermondii* species complex only, SojC recognizes *Candida sojae* only, Zeyla7 recognizes *Candida zeylanoides* only, Haemti3, Hem12, and HemC recognize *Candida haemulonii* only, Haemtii3, Hem22, and HemIIB recognize *Candida haemulonii* Type II only, TROP4, TROP5B, TROP8, TROP9, and to a lesser extent Trop6, recognize *Candida tropicalis* only with some low cross reactivity to *Candida sojae* and *Lodderomyces elongisporus*

Lelon2 recognizes *Lodderomyces elongisporus* only

Lusit2 recognizes *Clavispora lusitaniae* only,

Pcifer3 recognizes *Pichia ciferrii* only,

Fari2 recognizes *Stephanoascus farinosus* only,

Hellen2 recognizes *Zygoascus hellenicus* only, and

Malt5 recognizes *Candida maltosa* only.

In contrast, the following probes recognize the described species within the *C. albicans* clade:

Albclade5 recognizes *Candida neerlandica, Lodderomyces elongisporus, Candida parapsilosis, Candida* sp. n. NRRL Y-17456, *Candida sojae, Candida tropicalis*, and *Candida maltosa.*

Albclade3 recognizes *Candida neerlandica, Lodderomyces elongisporus, Candida parapsilosis, Candida* sp. n.

NRRL Y-17456, *Candida sojae, Candida tropicalis, Candida maltosa, Candida* lodderae, and *Candida viswanathii.*

Albclade4 recognizes *Candida albicans* and *Candida dubliniensis.*

Albclade8 recognizes *Candida albicans* and *Candida dubliniensis.*

Albclade9 recognizes *Candida albicans* and *Candida dubliniensis.*

Albclade10 recognizes *Candida lodderae, Candida viswanathii*, and some strains of *Candida albicans.*

A final clade probe recognizes yeast species within the *Debaryomyces hansenii* clade:

Hanclade3 recognizes *Candida natalensis, Debaryomyces maramus, Debaryomyces nepalensis, Debaryomyces hansenii* var. *hansenii, Debaryomyces hansenii* var. *fabryi, Candida psychrophila, Candida multigemmis, Debaryomyces udenii, Debaryomyces robertsiae*, and *Debaryomyces coudertii*. It is possible that the probe may also recognize *Debaryomyces etchellsii.*

Probe UniD serves as a positive control effective for recognizing virtually all ascomycetous yeats.

Oligonucleotides probes (or primers used in the PCR amplification of yeast DNA) may be synthesized chemically according to the solid phase phosphoramidite triester method described by Beaucage and Caruthers [1981, Tetrahedron Letts., 22(20):1859-1862], e.g., using an automated synthesizer, e.g., as described in Needham-VanDevanter et al. (1984, Nucleic Acids Res., 12:6159-6168). Other suitable techniques for synthesis of the oligonucleotide probes include those described, e.g., by Ozaki et al. (1992, Nucleic Acids Research, 20:5205-5214), Agrawal et al. (1990, Nucleic Acids Research, 18:5419-5423). The oligonucleotide probes of the invention are conveniently synthesized on an automated DNA synthesizer, e.g., an Applied Biosystems, Inc. (Foster City, Calif.) model 392 or 394 DNA/RNA Synthesizer, using standard chemistries, such as phosphoramidate chemistry, e.g., disclosed in the following references: Beaucage and Iyer (1992, Tetrahedron, 48:2223-2311), Molko et al. (U.S. Pat. No. 4,980,460), Koster et al. (U.S. Pat. No. 4,725,677), Caruthers et al. (U.S. Pat. Nos. 4,415,732, 4,458,066, and 4,973,679). The contents of each of the publications and patents referred to above are incorporated by reference herein. Alternative chemistries, e.g., resulting in non-natural backbone groups, such as phosphorothioate, phosphoramidate, and the like, may also be employed provided that the hybridization efficiencies of the resulting oligonucleotides and/or cleavage efficiency of the exonuclease employed are not adversely affected. Oligonucleotides can also be custom made and ordered from a variety of commercial sources. Purification of oligonucleotides, where necessary, is typically performed by either native acrylamide gel electrophoresis or by anion-exchange-HPLC as described in Pearson and Regnier (1983, J. Chrom. 255:137-149). The sequence of the synthetic oligonucleotides can be verified using the chemical degradation method of Maxam and Gilbert [1980, in Grossman and Moldave (eds.) Academic Press, New York, Methods in Enzymology, 65:499-560]. The contents of each of the above-mentioned publications are incorporated by reference herein.

The probes are used for the detection of pathogenic yeasts, particularly species in the clade of *C. albicans*, as well as other pathogenic ascomycetous yeasts, in a biological sample. These probes are specific for yeast species within the clade of *Candida albicans*, and may be used singly or in a multiplex hybridization assay system wherein the same sample of nucleic acid may be simultaneously or sequentially contacted with multiple probes. In brief, pathogenic yeast species in a biological sample may be detected by:
 a) recovering or releasing nucleic acid from the sample suspected of containing a pathogenic yeast,
 b) contacting the nucleic acid with one, or in the case of a multiplex system, a plurality of the detectably labeled oligonucleotide probes (to form a mixture of the probes and nucleic acid) under conditions effective to allow hybridization between the probes and complementary nucleic acids and form a probe/nucleic acid complex when one or more of the pathogenic yeasts are present, and
 c) detecting the presence or absence of probe/nucleic acid complexes as an indication of the presence of a pathogenic yeast.

It is envisioned that the hybridization assays can be performed without amplification of the rDNA of the target yeasts. However, in the preferred embodiment, after releasing the nucleic acids from the biological sample, the rDNA of the target pathogenic yeast will be amplified, for example, by PCR.

Thus, in a preferred embodiment, the assay includes the steps of:
 a) collecting biological sample,
 b) lysing any yeast cells therein,
 c) extracting and precipitating the rDNA from the lysed cells,
 d) amplifying the redissolved precipitated DNA using primer pairs universal for the D1/D2 region of the 28S rDNA (see the Examples), and
 e) detecting amplified DNA from the target yeast species by hybridizing the amplified DNA with one or more of the above-mentioned probes that selectively hybridize with the target yeast rDNA, the presence of amplified DNA indicating the presence of the target yeast species.

To facilitate detection of the complexes, the probes may be conjugated, covalently or non-covalently, with a variety of detectable labels known in the art, such as described by Sambrook et al. (Molecular Cloning, 2nd ed., Cold Spring Harbor Press, Plainview, N.Y., 1989, the contents of which are incorporated by reference herein). Useful labels include radioisotopes as well as non-radioactive reporting groups. Isotopic labels include $^3$H, $^{35}$S, $^{32}$P, $^{125}$I, $^{57}$Co, and $^{14}$C. Most methods of isotopic labeling involve the use of enzymes and include the known methods of nick translation, end labeling, second strand synthesis, and reverse transcription. When using radio-labeled probes, hybridization can be detected by autoradiography, scintillation counting, or gamma counting. The detection method selected will depend upon the hybridization conditions and the particular radio isotope used for labeling. Non-isotopic materials can also be used for labeling, and may be introduced internally into the sequence or at the end of the sequence. Modified nucleotides may be incorporated enzymatically or chemically and chemical modifications of the probe may be performed during or after synthesis of the probe, for example, by the use of non-nucleotide linker groups. Non-isotopic labels include fluorescent molecules, biotin-avidin, chemiluminescent molecules, enzymes, cofactors, enzyme substrates, haptens, mass-based labels or other ligands.

In a preferred embodiment, which is particularly suited to a multiplex assay system but is not limited thereto, the probes are conjugated to fluorescent beads (including microparticles and microcapsules). One particularly preferred multiplex hybridization assay system and fluorescent beads suitable for use therein, are described in Chandler et al. (U.S. Pat. Nos.

5,981,180, 6,632,526, 6,649,414, 6,268,222, 6,599,331, and 6,514,295) and Chandler (U.S. Pat. No. 6,528,165), the contents of each of which are incorporated by reference herein. In such a multiplex system, each probe is conjugated to a different fluorescent bead, such that the beads conjugated to any one probe have one or more different, characteristic classification parameters that distinguish them from beads conjugated to the other probes. Details of the beads and the techniques for conjugation to the probes are described hereinbelow. The skilled practitioner will recognize that multiplex assay systems can be performed with other labels as long as they can be independently differentiated from one another In one particularly preferred embodiment for use in a multiplex assay system, the oligonucleotide probes are labeled with the above-mentioned beads, while the target yeast rDNA is conjugated to biotin. Biotinylation may be effected during amplification as described hereinbelow. The biotinylated strand of the PCR product must be the strand that is complementary to the probe coupled to the beads. Following hybridization, the sample may be contacted with avidin, thereby allowing, for any bead having a given probe thereon, differentiation between beads having non-complexed probes vs. those having probe/target nucleic acid complexes. Alternatively, positive reactions (hybridized probes) may be detected using competitive inhibition hybridization assays as described in Chandler et al. (U.S. Pat. No. 5,981,180), supra.

Although the probes may be used in a multiplex assay in any desired combination, in the preferred embodiment the assay will at least include probes which are specific for yeasts of particular clinical significance, specifically *Candida albicans* (Alb7), *Candida tropicalis* (Trop5B), *Candida parapsilosis* (Parap2B and LPW), and *Candida glabrata* (Glab5). In a particularly preferred embodiment, one or both probes specific for *Pichia (Candida) guilliermondii* species complex (GG2 and GG3) are also included. Any or all of the other probes may also be optionally included, particularly one probe for *Candida dubliniensis* (Dub5) and/or one, preferably two, or more of the probes recognizing various members of the clade of *C. albicans* (Albclade5, Albclade3, Albclade4, Albclade8, Albclade9, and Albclade10). For detection and/or identification of *Candida* sp. n. NRRL Y-17456, use of probe SP12 is generally preferred over probe SP1.

The hybridization assay of this invention can be used to detect and/or identify pathogenic yeast species from a variety of biological specimens. In the preferred embodiment, biological samples will include yeast cultures or isolates from clinical specimens requiring identification or confirmation of identification of species. It is also envisioned that the assay may be performed directly upon clinical specimens such as blood, sputum, wound drainage, oral/esophageal swabs or scrapings, vaginal secretions, urine or excretia, or upon DNA extracted from infected tissue.

The probes of this invention may also be provided in one or more containers in a kit for the assays for detection of yeasts described herein. Such a kit may include a carrier being compartmentalized to receive in close confinement therein one or more containers, such as microtitre plates, tubes or vials. The labeled probes may be present in lyophilized form or in an appropriate buffer as necessary. Combinations of reagents useful in the methods set out above, particularly any of the probes and optional primers, can be packaged either singly or together with instructions for using them in the described assays. A preferred kit would contain the probes and instructions for performing the assay with a single test aliquot.

The following examples are intended only to further illustrate the invention and are not intended to limit the scope of the invention which is defined by the claims.

EXAMPLE 1

Probe Design

Probes were designed by aligning ascomycetous yeast DNA sequences of the D1/D2 region, and searching for species-specific DNA sequences. Probe sequences ranged from 15 bp to 25 bp in length. All probes were designed to place the sequence differences as close to the center of the probe as possible. Cross hybridization and probe interaction required the use of trial and error to re-design several probes so that they would work in a multiplex assay. The designed probes are optimized for hybridization assays. The probes can be modified with various reporters and used in a variety of detection systems.

Attachment of Probes to Beads:

5' amino modified primers with a 12 carbon linker were ordered from Integrated DNA Technologies and resuspended from dried pellets into water at a concentration of 1 mM stock solution each. Primers were then diluted 10:1 for a 100 µM concentration. Beads (obtained from the Luminex Corp., Austin, Tex., USA) were prepared by centrifugation of 200 µL of stock solution at 8000 RPM in bench top centrifuge for 1 minute. Supernatant storage buffer was decanted and beads were resuspended in 50 µL each 0.1 M MES (2[N morpholino] ethanesulfonic acid) and the pH of the solution adjusted to 4.5 using 5 N NaOH. Care was taken to expose the beads to as little light as possible, as accumulation of light causes photobleaching which prevents the Luminex hardware from registering the individual bead sets. Once resuspended, the beads were vortexed and 2 µL of 100 µM primer stock was added to each sample. Pre-weighed aliquots of dessicated EDC powder were warmed to room temperature. 1 mL of water was added to an EDC aliquot and immediately 2.5 µL of this solution was added to each sample. At room temperature EDC drives the chemical reaction that fuses the amino modified primers to the carboxylated beads. Because EDC is only stable for a short while after it is hydrated, the immediate addition of the chemical after combined water is crucial for good coupling reactions. The samples were incubated in the dark at room temperature for 30 minutes. Following this incubation step, a second aliquot of EDC was combined with 1 mL of water and 2.5 µL per sample was added. Another incubation at room temperature in the dark for 30 minutes was performed. After incubation with EDC, 1 mL of 0.02% TWEEN was added and the samples were vortexed and then centrifuged at 8000 RPM for 1 minute on a table top centrifuge. The supernatant was aspirated taking care to not disturb the pelleted beads. 1 mL of 0.1% SDS was then added. The samples were vortexed and then centrifuged again at 8000 RPM for 1 minute in a table top centrifuge. The supernatant was once again aspirated taking care to not disturb the pelleted beads. The beads were then resuspended in water and a dilution stock of 100:1 was made in order to count the number of beads per µL on a hemacytometer. Beadsets with the newly attached primers were then stored at 4° C. for future use.

Growth of Cultures and DNA Isolation:

Growth of yeast cultures and extraction of rDNA therefrom were performed using substantially the same techniques described in Kurtzman and Robnett (2003, FEMS Yeast Research, 3:417-432, the contents of which are incorporated by reference herein).

Cells used for DNA extraction were grown for approximately 24 h at 25° C. in 50 mL of Wickerham's YM broth (1951, Taxonomy of Yeasts, USDA Tech. Bull. 1029, Washington, D.C.) (3 g yeast extract, 3 g malt extract, 5 g peptone, and 10 g glucose per liter of distilled water) on rotary shaker at 200 rpm and harvested by centrifugation. The cells were washed once with distilled water, resuspended in 2 mL of distilled water and aliquoted to two 1.5 mL microcentrifuge tubes. After centrifugation, excess water was decanted from the microfuge tubes, and the packed cells were freeze dried for 1-2 days and stored at −20° C. until used. DNA isolation for polymerase chain reaction (PCR) was performed using either the sodium dodecyl sulfate method of Raeder and Broda or the CTAB (hexadecyltrimethyl ammonium bromide) procedure, both of which are described in detail by Kurtzman and Robnett (1998, Antonie van Leeuwenhoek, 73:331-371, the contents of which are incorporated by reference herein).

DNA isolation was performed by a modified version of the sodium dodecyl sulfate protocol of Raeder and Broda (1985, Lett. Appl. Microbiol., 1:17-20, the contents of which are incorporated by reference herein). The lyophilized cell mass from a single 1.5 mL microcentrifuge tube was broken apart with a pipette tip, and ca. 0.5 mL of 0.5 mm diameter glass beads was added to the microfuge tube. The tube was shaken for 20 min on a wrist action shaker at maximum speed. This treatment visibly fractured about 25% of the cells. The cells were suspended in 1 mL of extraction buffer (200 mM Tris HCl [pH 8.5], 250 mM NaCl, 25 mM EDTA [pH 8.0], 0.5% sodium dodecyl sulfate) and extracted with phenol chloroform and chloroform. As an alternative to the laboratory use of phenol, the broken cells were suspended in 700 µL 2×CTAB buffer (100 mM Tris HCl [pH 8.4], 1.4 M NaCl, 25 mM EDTA, 2% hexadecyltrimethyl ammonium bromide), vortex mixed with an equal volume of chloroform and centrifuged for 10 min. Following either extraction procedure, DNA was precipitated from aqueous phase by adding 0.54 volume of isopropanol and pelleted for ca. 3 min in an Eppendorf model 5415 microcentrifuge at 14,000 rpm. The pellet was washed gently with 70% ethanol, resuspended in 100 µL of TE buffer (10 mM Tris HCl, 1 mM EDTA [pH 8.0]), and dissolved by incubation at 55° C. for 1 to 2 hours. Dilute DNA samples for PCR were prepared by adding 4 µL of the genomic stocks to 1 ml of 0.1×TE buffer.

Hybridization of Beadsets/Probes with PCR Products:

PCR conditions are specific to each specific amplicon. The D1/D2 region of the rDNA is approximately 600 bp long and can be amplified using the primers NL1 (5' GCATATCAATAAGCGGAGGAAAAG3') (SEQ ID no. 21) and NL4 (5' GGTCCGTGTTTCAAGACGG3') (SEQ ID no. 22). To allow subsequent detection of hybridized probe/target DNA complexes, the target DNA is biotinylated. In this example, in preparation for hybridization, the 3' primer relative to the probe direction is biotinylated, although either or both NL1 and NL4 can be biotinylated in the PCR reaction. PCR for the D1/D2 region using NL1 and NL4 as PCR primers is carried out using an initial 2 minute 94° C. step for denaturation of the DNA molecules, followed by a 30 second 94° C. denaturation step, a 30 second 55° C. annealing step, and then a 1 minute 72° C. extension step. Steps 2-4 are repeated 40 additional times, and then a final 8 minute extension step is carried out before storage of the PCR products at 4° C. or −20° C. The number of cycles or repetitions of steps 2-4 can be variable from as little as 20 cycles to 40 cycles or more. The extension step carried out at 72° C. can range from 30 seconds to 2 minutes long, and the annealing temperature of 52-55° C. (can range from 45° C. to 60° C.).

For the hybridization step, 1-15 µL of PCR product may be used in a total volume of 17 µL of water. Beadsets with probes attached are diluted so that approximately 2500 beads with attached probes per bead set are used in each sample well. The number of beads per well may be variable and can range from 500 beads to 5000 beads. The bead sets are diluted using 1.5×TMAC solution containing 4.5 M TMAC, 0.15% sarkosyl, 75 mM Tris HCl pH 8.0, and 6 mM EDTA pH 8.0, so that 33 µL of 1.5×TMAC containing the appropriate amount of beads is added to each sample well. The mixture of beads and PCR product is mixed together by pipetting up and down and then incubated in the dark at an initial denaturation temperature of 96° C. for 5 minutes followed by 15 minutes incubation in the dark at a set temperature between 45° C. and 60° C. This incubation step is followed by the addition of 12-25 µL per well of 1×TMAC solution containing 10 ng/µL streptavidin and incubating for 5-15 minutes in the dark at the hybridization temperature. Samples are then measured based on fluorescence intensity in the LUMINEX 100 Flow cytometer.

EXAMPLE 2

The assay may be performed using rRNA using substantially the same procedures as described in Example 1 except for the extraction and purification of the nucleic acids. rRNA may be extracted and purified for assay using the techniques described by Kurtzman and Robnett (1991, Yeast, 7:61-72, the contents of which are incorporated by reference herein).

Cultures were grown at 25° C. in 100 ml of YM medium on rotary shaker at 200 rpm for ca. 16 h. Cells were harvested by centrifugation, suspended 1 g wet weight/10 ml of buffer containing 4 M guanidinum thiocyanate and broken in a Braun cell homogenizer with 0.5 mm glass beads. The guanidinium thiocyanate buffer and the remainder of the isolation procedure are described in Chirgwin et al. (1979, Biochemistry, 18:5284-5299, the contents of which are incorporated by reference herein). Undegraded rRNA, as assessed from nondenaturing agarose gel electrophoresis, was obtained by this method. Sequencing of rRNA was obtained using specific oligonucleotide primers and the dideoxy nucleotide chain termination method.

It is understood that the foregoing detailed description is given merely by way of illustration and that modifications and variations may be made therein without departing from the spirit and scope of the invention.

We claim:

1. A method for detecting yeast species comprising one or more of *Candida albicans, Candida tropicalis, Lodderomyces elongisporus* and *Candida glabrata*, in a biological sample comprising:

a) recovering nucleic acid from said biological sample, b) contacting said nucleic acid with a plurality of oligonucleotide probes under conditions effective to allow hybridization between said probes and complementary nucleic acids to form a probe/nucleic acid complex when one or more of said yeasts are present, wherein said plurality of probes comprises:

(1) Alb7 or an oligonucleotide complementary thereto,
   (2) Trop5B or an oligonucleotide complementary thereto,
   (3) LPW or an oligonucleotide complementary thereto, and
   (4) Glab5 or an oligonucleotide complementary thereto, and further wherein each of said probes are detectably labeled, and c) detecting the presence or absence of said probe/nucleic acid complexes as an indication of the presence of a yeast comprising one or more of said *Candida albicans, Candida tropicalis, Lodderomyces elongisporus* and *Candida glabrata*.

2. The method of claim 1 wherein said biological sample comprises yeast cultures, yeast isolates, blood, sputum, wound drainage, oral/esophageal swabs or scrapings, vaginal secretions, urine or excretia.

3. The method of claim 1 wherein each of said probes are independently detectable and can be differentiated from one another.

4. The method of claim 3 wherein said probes are labeled by conjugation with fluorescent beads, said beads which are conjugated to any one of said probes have one or more different, characteristic classification parameters that distinguish those beads from beads conjugated to other of said probes.

5. The method of claim 1 wherein said nucleic acid is contacted with all of said probes simultaneously.

6. The method of claim 1 wherein said nucleic acid from said sample comprises rDNA.

7. The method of claim 6 wherein recovering comprises releasing nucleic acids from said biological sample and amplifying rDNA of said yeast therein.

8. The method of claim 6 wherein said rDNA is amplified by PCR.

9. The method of claim 6 wherein said rDNA is from the D1/D2 region of rDNA.

10. The method of claim 1 wherein said plurality of probes further comprises one or both of probes GG3 and GG2, or oligonucleotides complementary thereto.

11. The method of claim 1 wherein said plurality of probes further comprises one or more additional oligonucleotide probes which hybridize to the clade of *Candida albicans*.

12. The method of claim 11 wherein said additional probes comprise Albclade5, Albclade3, Albclade4, Albclade8, Albclade9, and Albclade10, or oligonucleotides complementary thereto.

13. The method of claim 1 wherein said plurality of probes further comprises one or more additional oligonucleotide probes, said additional probes comprising Dub5, SP1, SP12, Lod2, Nee5, Soj7, Malt5, Lelon7, Lelon2, Krusei5, Zeyla1, HaemtI3, HaemtII3, Hem22, and Hem12, HemC, HemIIB, Pcifer3, Lusit2, Fari2, Hellen2, KrusF, SojC or oligonucleotides complementary thereto.

14. The method of claim 13 wherein said additional probes comprise one or more of said Trop6, Trop4, Trop5, Trop8, and Trop9, or oligonucleotides complementary thereto.

15. The method of claim 3 wherein the detection of the presence of a nucleic acid complex with said Alb7 or oligonucleotide complementary thereto indicates the presence of said *Candida albicans*, the detection of the presence of a nucleic acid complex with said Trop5B or oligonucleotide complementary thereto indicates the presence of *Candida tropicalis*, the detection of the presence of nucleic acid complexes with both of said Trop5B and LPW or oligonucleotides complementary thereto indicates the presence of *Lodderomyces elongisporus*, and the detection of the presence of a nucleic acid complex with said Glab5 or oligonucleotide complementary thereto indicates the presence of *Candida glabrata*.

16. The method of claim 1 wherein said plurality of probes further comprises Parap2B or an oligonucleotide complementary thereto, and said detecting the presence or absence of said probe/nucleic acid complexes provides an indication of the presence of a yeast comprising one or more of said *Candida albicans, Candida tropicalis, Lodderomyces elongisporus, Candida glabrata*, and *Candida parapsilosis*.

17. The method of claim 16 wherein each of said probes are independently detectable and can be differentiated from one another.

18. The method of claim 17 wherein the detection of the presence of a nucleic acid complex with said Alb7 or oligonucleotide complementary thereto indicates the presence of said *Candida albicans*, the detection of the presence of a nucleic acid complex with said Trop5B or oligonucleotide complementary thereto indicates the presence of *Candida tropicalis*, the detection of the presence of nucleic acid complexes with both of said Trop5B and LPW or oligonucleotides complementary thereto indicates the presence of *Lodderomyces elongisporus*, the detection of the presence of a nucleic acid complex with said Glab5 or oligonucleotide complementary thereto indicates the presence of *Candida glabrata*, and the detection of the presence of nucleic acid complexes with both of said Parap2B and LPW or oligonucleotides complementary thereto indicates the presence of *Candida parapsilosis*.

19. The method of claim 1 wherein said biological sample comprises a yeast culture or yeast isolate.

20. The method of claim 15 wherein said biological sample comprises a yeast culture or yeast isolate.

21. The method of claim 16 wherein said biological sample comprises a yeast culture or yeast isolate.

22. The method of claim 18 wherein said biological sample comprises a yeast culture or yeast isolate.

* * * * *